(12) United States Patent
Yoshioka et al.

(10) Patent No.: US 9,433,540 B2
(45) Date of Patent: Sep. 6, 2016

(54) DISPOSABLE PULL-ON DIAPER HAVING INTERIOR ELASTIC SHEETS AND EXTERIOR NON-ELASTIC SHEETS

(75) Inventors: Toshiyasu Yoshioka, Kagawa (JP); Seiichi Kuwano, Kagawa (JP)

(73) Assignee: Unicharm Corporation, Ehime (JP)

( * ) Notice: Subject to any disclaimer, the term of this patent is extended or adjusted under 35 U.S.C. 154(b) by 372 days.

(21) Appl. No.: 13/983,349

(22) PCT Filed: Jan. 20, 2012

(86) PCT No.: PCT/JP2012/051153
§ 371 (c)(1),
(2), (4) Date: Aug. 2, 2013

(87) PCT Pub. No.: WO2012/105332
PCT Pub. Date: Aug. 9, 2012

(65) Prior Publication Data
US 2013/0317468 A1    Nov. 28, 2013

(30) Foreign Application Priority Data

Feb. 2, 2011    (JP) ................. 2011-021250

(51) Int. Cl.
*A61F 13/15* (2006.01)
*A61F 13/20* (2006.01)
*A61F 13/49* (2006.01)
(Continued)

(52) U.S. Cl.
CPC ... *A61F 13/49019* (2013.01); *A61F 13/15593* (2013.01); *A61F 13/15699* (2013.01); *A61F 13/42* (2013.01); *A61F 13/4902* (2013.01);
(Continued)

(58) Field of Classification Search
CPC .................. A61F 13/49007; A61F 13/49009; A61F 13/49011; A61F 2013/49007; A61F 2013/49009; A61F 2013/49036
USPC ....................... 604/385.24, 385.27
See application file for complete search history.

(56) References Cited

U.S. PATENT DOCUMENTS 6,554,815 B1    4/2003    Umebayashi
2005/0234414 A1*   10/2005   Liu .................. A61F 13/42
                                                 604/361

(Continued)

FOREIGN PATENT DOCUMENTS

JP    06-197925    7/1994
JP    06-254117    9/1994
(Continued)

OTHER PUBLICATIONS

International Search Report based on corresponding PCT application No. PCT/JP2012/051153 dated Apr. 10, 2012 (4 pgs).

*Primary Examiner* — Michele M Kidwell
(74) *Attorney, Agent, or Firm* — Brinks Gilson & Lione

(57) ABSTRACT

A disposable pull-on diaper having a central inelastic region in at least one of a front waist region and a rear waist region, and a method for manufacturing the same. Front and rear waist regions of a disposable pull-on diaper are respectively of an elastically non-stretchable exterior sheet and elastically stretchable interior sheets. In lateral elastic regions of this waist region, the interior sheets are attached under tension to an interior surface of the exterior sheet and, in a central inelastic region, the interior sheets are spaced apart from each other in a transverse direction and regions of the interior sheets are in an elastically contracted and relaxed state in vicinities of the lateral elastic regions.

16 Claims, 9 Drawing Sheets

(51) Int. Cl.
*A61F 13/494* (2006.01)
*A61F 13/42* (2006.01)

(52) U.S. Cl.
CPC ... *A61F 13/49058* (2013.01); *A61F 13/49413* (2013.01)

(56) References Cited

U.S. PATENT DOCUMENTS

| | | | | |
|---|---|---|---|---|
| 2007/0287975 | A1* | 12/2007 | Fujimoto | A61F 13/49011 604/385.3 |
| 2011/0077609 | A1* | 3/2011 | Kuwano | A61F 13/49011 604/385.01 |
| 2011/0172626 | A1* | 7/2011 | Mitsuno | A61F 13/49011 604/385.3 |

FOREIGN PATENT DOCUMENTS

| | | |
|---|---|---|
| JP | 6-77721 | 11/1994 |
| JP | 2001-478 A | 1/2001 |
| JP | 2001-145666 | 5/2001 |
| JP | 2011-286504 | 10/2001 |
| JP | 2002-505913 A | 2/2002 |
| JP | 2008-148943 | 7/2008 |
| JP | 2010-233733 A | 10/2010 |
| WO | WO 99/45880 | 9/1999 |
| WO | WO 2010/113472 A1 | 10/2010 |
| WO | 2011/024489 A1 * | 3/2011 ............. A61F 13/15 |

* cited by examiner

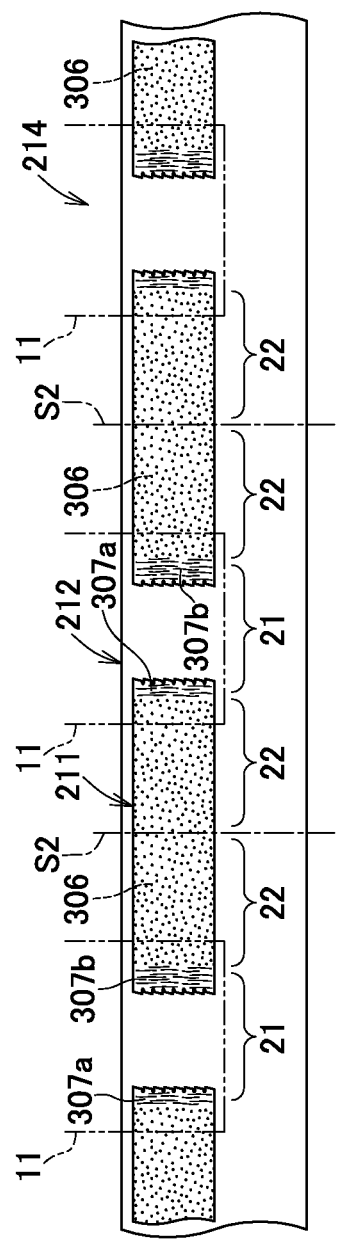

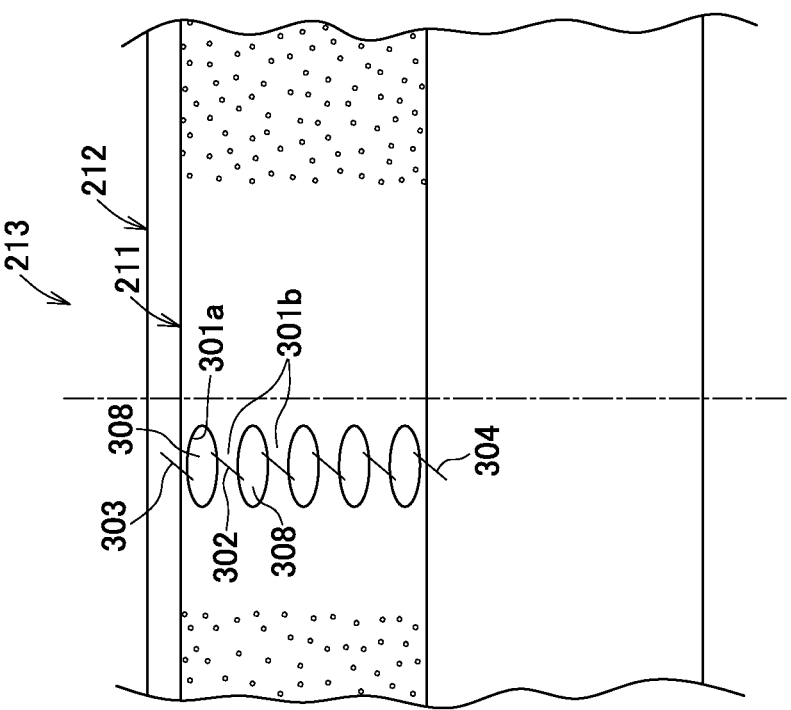

DISPOSABLE PULL-ON DIAPER HAVING INTERIOR ELASTIC SHEETS AND EXTERIOR NON-ELASTIC SHEETS

RELATED APPLICATION

This application is a 35 U.S.C. §371 national phase filing of International Patent Application No. PCT/JP2012/051153, filed Jan. 20, 2012, through which and to which priority is claimed under 35 U.S.C. §119 to Japanese Patent Application No. 2011-021250, filed Feb. 2, 2011.

TECHNICAL FIELD

The present invention relates to disposable pull-on diapers and methods for manufacturing the same.

BACKGROUND

Disposable pull-on diapers are known having front and rear waist regions at least one of which is elastically stretchable in the circumferential direction. Other disposable diapers are also known having a midsection of a waist region overlapping with a body exudates absorbent structure which includes none of elastics under tension and lateral regions of the body exudates absorbent structure which include elastics under tension so that the midsection is not formed with gathers/creases and the lateral regions are formed with gathers/creases.

For example, JP 2001-145666 A (PTL 1) discloses a disposable pull-on diaper as an example of the absorbent article and, in this disposable pull-on diaper, waist elastics are attached under tension to a region in which no absorbent body is present so that an elasticity may develop and the waist elastics are cut without being attached to a region in which the absorbent body is present so that the elasticity may substantially not develop and none of gathers/creases may be formed.

In a method for manufacturing the absorbent article disclosed in JP 2001-286504 A (PTL 2), waist elastics are interposed between a pair of exterior sheets. The waist elastics for a region in which the absorbent body is not present are secured. The waist elastics for a region in which the absorbent body is present are cut and secured with a heat processing and a pressure processing.

CITATION LIST

Patent Literature

{PTL 1}: JP 2001-145666 A
{PTL 2}: JP 2001-286504 A

SUMMARY

Technical Problem

In the absorbent article disclosed in PTL 1, the waist elastics are not attached to the other members and cut together with an elastic fixing sheet and an auxiliary sheet in the region wherein the absorbent body is present. Consequently, these two sheets are inevitably formed with a large opening extending in a direction intersecting with all the waist elastics. In addition, it is required to provide a shield sheet to cover the opening and disordered cut ends of the waist elastics.

The manufacturing method disclosed in PTL 2 is not applicable to belt-like waist elastics having a large width dimension.

An object of the present invention is to provide a disposable pull-on diaper and a method for manufacturing the same improved to solve these problems of prior art.

Solution to Problem

The present invention to solve the problems set forth above includes a first aspect relating to a disposable pull-on diaper and a second aspect relating to a method for manufacturing the same.

The present invention on the first aspect thereof relates to a disposable pull-on diaper having a longitudinal direction and a transverse direction being orthogonal to the longitudinal direction and including a front waist region, a rear waist region, a crotch region, an absorbent chassis extending from the crotch region to the front and rear waist regions, lateral elastic regions formed in at least one of the front and rear waist regions so as to be elastically stretchable in the transverse direction from lateral edges of the absorbent chassis and a central inelastic region defined between the lateral elastic regions and not being stretchable either elastically or inelastically.

At least one of the front and rear waist regions includes an exterior sheet which is not elastically stretchable in the transverse direction and an interior sheets which lie on an interior surface side of the exterior sheet and is elastically stretchable in the transverse direction. The interior sheets are contractibly attached under tension to the interior surface of the exterior sheet in the lateral elastic regions. In the central inelastic region, the interior sheets are spaced apart from each other in the transverse direction and in an elastically relaxed state in vicinities of the respective lateral elastic regions.

According to an embodiment of the present invention on the first aspect thereof, the central inelastic region is formed on an exterior side of the absorbent chassis.

According to another embodiment of the present invention on the first aspect thereof, the absorbent chassis has lateral edge portions on lateral sides of a longitudinal axis bisecting the diaper in the transverse direction and the lateral edge portions are attached to the lateral elastic regions.

According to even another embodiment of the present invention on the first aspect thereof, the absorbent chassis has a barrier sheet and the central inelastic region is attached to the absorbent chassis from an exterior side of the barrier sheet.

According to still another embodiment of the present invention on the first aspect thereof, an indicator adapted to indicate an occurrence of urination within the diaper is interposed between the central inelastic region and the absorbent chassis.

According to yet another embodiment of the present invention on the first aspect thereof, graphic display sheets are attached to the interior surface of the exterior sheet and the graphics are visually recognizable from the outside of the exterior sheet.

According to further another embodiment of the present invention on the first aspect thereof, the interior sheets are formed of an elastically stretchable elastic fibrous nonwoven fabric of an elastically stretchable elastic material and an elastically non-stretchable inelastic material.

According to even further another embodiment of the present invention on the first aspect thereof, the interior sheets are formed of a nonwoven fabric formed of thermoplastic synthetic fibers and a plurality of rubber thread or rubber bands being contractibly attached under tension to the nonwoven fabric.

According to still further another embodiment of the present invention on the first aspect thereof, the interior sheets are formed of a thermoplastic synthetic resin film which is elastically stretchable in the transverse direction.

The present invention on the second aspect thereof relates to a method for manufacturing a disposable pull-on diaper having a longitudinal direction and a transverse direction being orthogonal to the longitudinal direction, including a front waist region, a rear waist region, a crotch region, an absorbent chassis extending from the crotch region to the front and rear waist regions, lateral elastic regions formed in at least one of the front and rear waist regions so as to be elastically stretchable in the transverse direction from lateral edge portions of the absorbent chassis and a central inelastic region defined between the lateral elastic regions and not being stretchable elastically or inelastically.

The present invention on the second aspect thereof includes the following steps:

a. continuously feeding a first web which is elastically stretchable in a machine direction in a state under tension in the machine direction;

b. forming the first web with series of cut lines each including a plurality of cut lines extending in parallel to each other and arranged in a cross direction intersecting with the machine direction so as to be spaced apart from each other at predetermined intervals and forming a plurality of the series of cut lines arranged in the machine direction at a pitch corresponding to a dimension in the transverse direction of the diaper to obtain a first processed web from the first web;

c. feeding a second web which is not elastically stretchable in the machine direction in a tensioned state in the machine direction;

d. lapping the first processed web over the second web, forming a joint region defined between each pair of the adjacent series of cut lines in which the first web and the second web are joined to each other and a non-joint region in a region in which the series of cut lines is formed and regions adjacent thereto in which the first processed web and the second processed web are not joined to each other and, in this way, obtaining a second processed web from the first processed web and the second web;

e. in the series of cut lines of the first processed web lapped over the second processed web, forming second cut lines intersecting with each pair of the adjacent first cut lines in the cross direction and third cut lines intersecting with the first cut lines lying adjacent to lateral edges of the first processed web in the machine direction, respectively, wherein the region of the first processed web in which the series of cut lines is formed is bisected in the machine direction and second and third regions lying on lateral sides of the region in the machine direction are left to contract in directions opposite to each other to obtain a third processed web;

f. bonding a portion of the absorbent chassis to the third processed web; and g. after the step f, cutting the third processed web at a center of the joint region in the machine direction to form the lateral elastic regions from a portion of the joint region in the third processed web and forming the central inelastic region from the region in which the series of cut lines are formed.

According to an embodiment of the present invention on the second aspect thereof, the first web is an elastically stretchable nonwoven fabric formed of elastic yarns/threads and inelastic yarns/threads not being elastically stretchable.

According to another embodiment of the present invention on the second aspect thereof, the first web is formed of a nonwoven fabric of thermoplastic synthetic fibers and a plurality of rubber threads or rubber bands being elastically elongated in the machine direction and contractibly attached under tension to the nonwoven fabric.

According to still another embodiment of the present invention on the second aspect thereof, the first web is formed of a thermoplastic synthetic resin film which is elastically stretchable in the machine direction.

Advantageous Effects of Invention

According to the present invention on the first aspect thereof, at least one of the front and rear waist regions is formed of the elastically non-stretchable exterior sheet and the elastically stretchable interior sheets. The interior sheets are attached under tension to the interior surface of the exterior sheet in the lateral elastic regions of the respective waist regions. The interior sheets are spaced apart from each other in the transverse direction on lateral sides of the central inelastic region and in an elastically relaxed state in the vicinity of the lateral elastic regions. Consequently, the interior sheets in the relaxed state are less-visible from the outside through the exterior sheet and the diaper should not be disfigured.

According to the present invention on the second aspect thereof, in the second processed web of the first web in the elastically stretched state and the elastically non-stretchable second web under tension, the second and third cut lines intersecting with a plurality of first cut lines of the first processed web and spaced apart from each other are formed and the first processed web is cut in the region defined by the first cut lines. In consequence, the second web in the second processed web may be used as the central inelastic region lying on the exterior side of the absorbent chassis since the region of the second processed web corresponding to the region of the first processed web defined by the first cut lines should not elastically contract in the transverse direction.

BRIEF DESCRIPTION OF DRAWINGS

FIG. 9 is a diagram partially illustrating a fourth processed web.

FIG. 10 is a partially scale-enlarged diagram illustrating a series of cut lines according to an embodiment.

DESCRIPTION OF EMBODIMENTS

Details of the present invention will be described hereunder with reference to the accompanying drawings.

Figure 1:
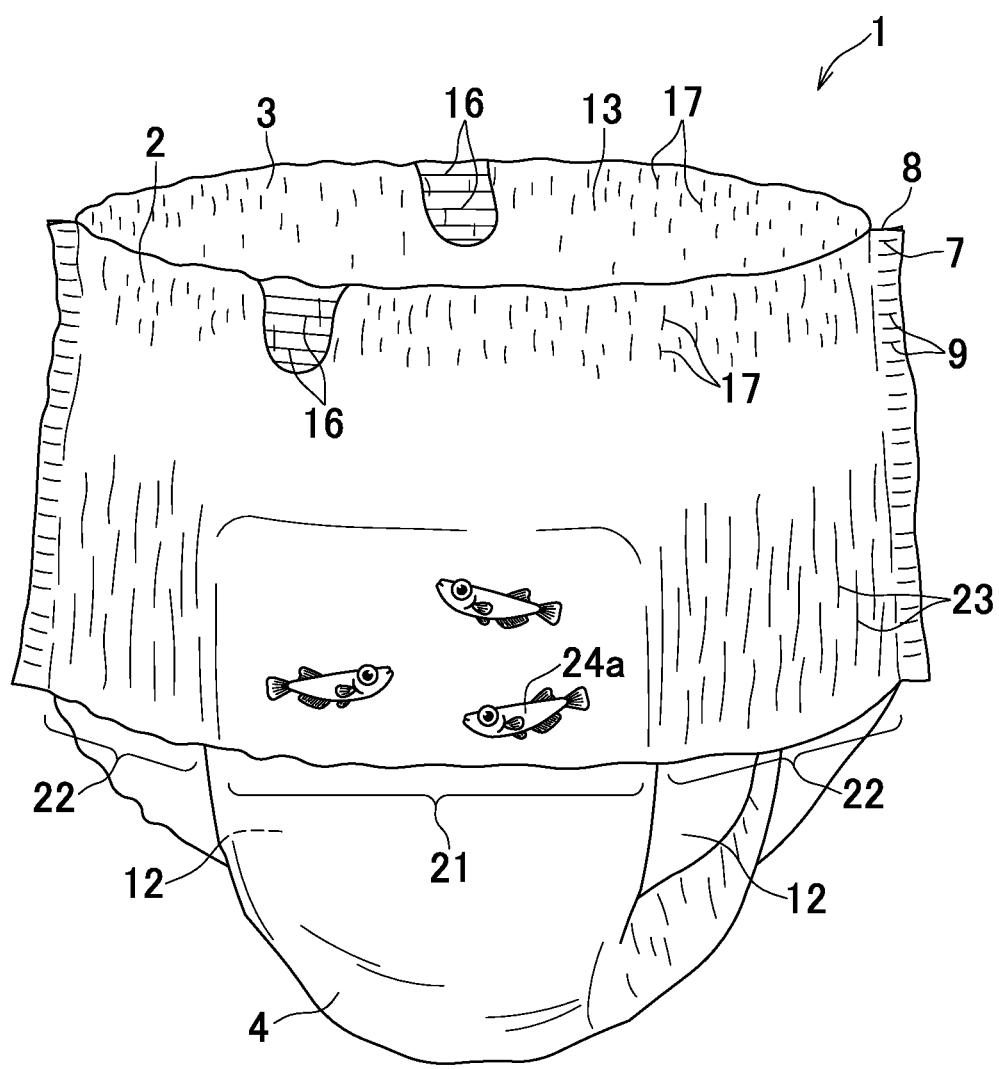
FIG. 1 is a partially cutaway perspective view of a disposable pull-on diaper.

Referring to FIG. 1 which is a perspective view of a diaper 1, the diaper 1 has a front waist region 2, a rear waist region 3 and a crotch region 4 wherein the front and rear waist regions 2, 3 have respective inner surfaces of lateral edge portions 7, 8 put flat and welded together at a series of seams 9 arranged at intervals in a longitudinal direction and the front and rear waist regions 2, 3 should not be readily peeled off each other during use of the diaper 1. The crotch region 4 is formed of an absorbent chassis 11 extending from the crotch region 4 toward the front waist region 2 and the rear waist region 3. Lateral sides of the crotch region 4 define leg-openings 12 and the front and rear waist regions 2, 3 define a waist-opening 13. A periphery of the waist-opening 13 defined by the front and rear waist regions 2, 3 is formed with gathers 17 under contraction of waist elastics to be described later. The front waist region 2 has a central inelastic region 21 defined by a midsection in a transverse direction B of the diaper 1 and overlapping with the absorbent chassis 11 and lateral elastic regions 22 defined on lateral sides in the transverse direction B of the absorbent chassis 11 wherein the central inelastic region 21 is formed with substantially none of gathers/creases and graphics of fish 24a displayed thereon are correspondingly clear. The lateral elastic regions 22 are formed with many gathers/creases due to contraction of the front waist region 2 in the transverse direction B. In FIG. 1, a front-back direction and a longitudinal direction of the diaper are respectively indicated by double-headed arrows A, C. In this regard, the transverse direction B will be sometimes referred to hereunder as a waist circumference direction.

Figure 2:
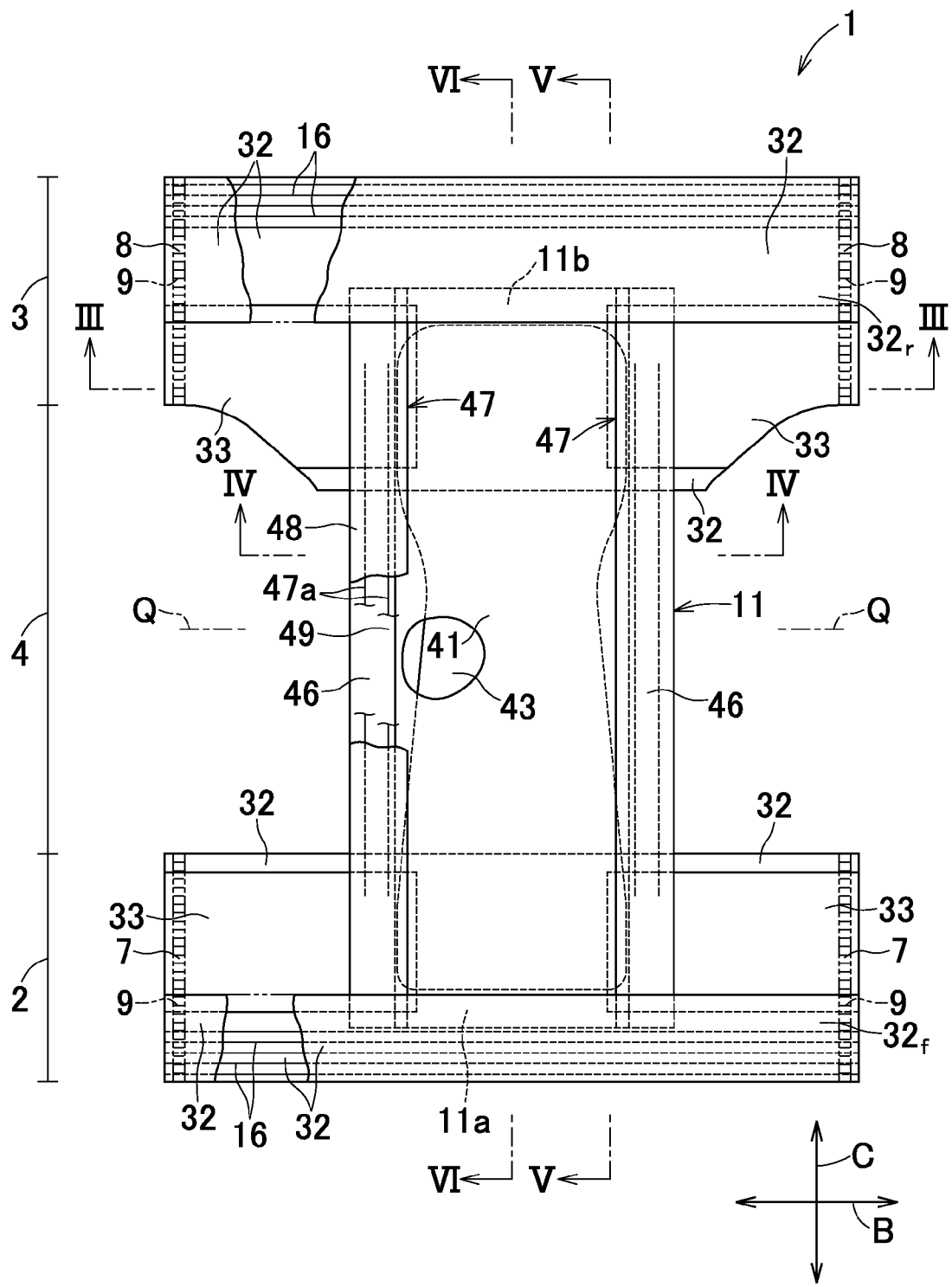
FIG. 2 is a partially cutaway plan view of the developed diaper.

FIG. 2 is a partially cutaway plan view of the diaper 1 flatly developed from the state in FIG. 1 after the joint along the series of seams have been released. The front waist region 2 and the rear waist region 3 are respectively formed of exterior sheets 32 and interior sheets 33 joined to an interior surface of the exterior sheets 32 with a hot melt adhesive (not shown) wherein end portions 32f, 32r of the exterior sheets 32 are folded along a periphery of the waist-opening 13 (See FIG. 1) inwardly of the diaper 1 so as to cover front and rear end portions 11a, 11b of the absorbent chassis 11. Between the respective folded end portions 32f, 32r and portions of the exterior sheets 32 facing these folded end portions 32f, 32r, a plurality of the waist elastics 16 are interposed and contractibly attached under tension with a hot melt adhesive (not shown). The exterior sheets 32 are formed of a nonstretchable sheet material which is elastically nonstretchable in the transverse direction, preferably nonstretchable inelastically also. As such sheet material, for example, a spunbonded fibrous nonwoven fabric, a spunbonded/meltblown/spunbonded fibrous nonwoven fabric (SMS fibrous nonwoven fabric) or air-through nonwoven fabric, each having a mass per unit area in a range of 10 to 40 g/m², more preferably in a range of 15 to 30 g/m² may be used.

The interior sheets 33 are formed of a sheet material which is elastically stretchable and contractible in the transverse direction B, and the respective interior sheets 33 in a state stretched so as to become 1.5 to 3.5 times, more preferably 2 to 2.8 times of a dimension $L_0$ (not shown) in the transverse direction B of the contracted and relaxed interior sheets 33, in other words, in a state stretched by 50 to 250% of the dimension $L_0$ are attached to the exterior sheets 32 at a mass per unit area in a range of 2 to 4 g/m² with a hot melt adhesive (not shown) to form the lateral elastic regions 22. The hot melt adhesive is distributed to at least one of the surfaces to be joined to each other. In this regard, an elongation ratio of the interior sheets in FIG. 2 is a value obtained in the form of a ratio between L and $L_0$, i.e., $L/L_0$ wherein L represents a dimension of the respective interior sheets 33 in the state illustrated in FIG. 2 and $L_0$ represents a dimension of the respective interior sheets 33 in a contracted state after peeled off the exterior sheets 32. As material for the elastically stretchable and contractible interior sheets 33, for example, a nonwoven fabric formed of elastically stretchable and contractible fibers, such as an elastically stretchable and contractible air-through nonwoven fabric or a spunbonded nonwoven fabric formed of fusion-bonding elastomeric fibers and having a mass per unit area in a range of 15 to 50 g/m², more preferably in a range of 25 to 40 g/m² may be used. Considering that the interior sheets 33 come in contact with the wearer's skin (not shown), a fibrous nonwoven fabric used as the interior sheets 33 are preferably flexible, and preferably the elastomeric fibers or the fibers mixed with or laminated with the elastomeric fibers are mechanically entangled and fusion-bonded. This is because the nonwoven fabric processed in this manner is generally more flexible and less apt to irritate the wearer's skin than a fibrous nonwoven fabric made with use of a binder.

The absorbent chassis 11 includes an absorbent structure 40 having a panel-like absorbent core material 43 interposed between a liquid-permeable sheet 41 and a barrier sheet 42 and a base sheet 44 formed of a thermoplastic synthetic fiber nonwoven fabric attached to an exterior surface of the barrier sheet 42 to provide the exterior surface of the absorbent chassis 11 with a cloth-like texture wherein the absorbent chassis 11 is disposed along lateral edges thereof with barrier cuffs 47. The barrier cuffs 47 are formed of substantially liquid-impermeable fibrous nonwoven fabrics respectively being folded inwardly. The barrier cuffs 47 respectively have proximal edge portions 48 attached to the barrier sheet 42 and the base sheet 44 and distal edge portions 49 doubled up and adapted to be spaced away from the absorbent structure toward the wearer's skin. The doubled up distal edge portions of the respective barrier cuffs 47 include, between the respective doubled up layers thereof, elastics 47a attached under tension in the longitudinal direction A and, upon contraction of the elastics 47a, the distal edge portions 49 are spaced away upward (toward the wearer's body) from the absorbent structure 40.

Figure 3:
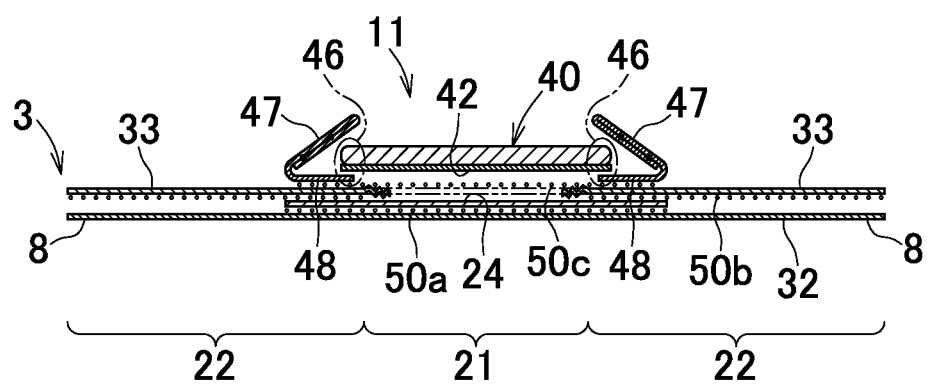
FIG. 3 is a sectional view taken along line III-III in FIG. 2.

FIG. 3 is a sectional view taken along line III-III in FIG. 2. The rear waist region 3 includes the exterior sheet 32, a graphic display sheet 24 attached to the interior surface of the exterior sheet 32 with a hot melt adhesive 50a in the central region as viewed in the transverse direction B and the interior sheet 33 attached to the lateral edge portions of the exterior sheet 32 with a hot melt adhesive 50b. The exterior sheet 23 and the interior sheet 33 extend in the transverse direction B to the lateral edges 8 and heat sealed along the series of seams 9 (See FIGS. 1 and 2). In this regard, the seams 9 are not illustrated in FIG. 3. In FIG. 3 and FIGS. 4 to 6, some of the elements actually in contact with each other are illustrated to be spaced apart from each other so that the respective elements such as the exterior sheet 32 and the respective hot melt adhesives may be clearly illustrated. The interior sheet 33 are contractibly attached under an elastic tension in the transverse direction B to the exterior sheet 32 and a graphic display sheet 24 and assembled with these sheets 32, 24 to form the lateral elastic regions 22. Referring to FIG. 7, in the central region as viewed in the transverse direction B, the interior sheets 33 are not in a stretched state but in a relaxed state and not joined to the exterior sheets 32 and the graphic display sheets 24. In the central region, the exterior sheets 32 and the graphic display sheets 24 joined to the exterior sheets 32 form the central inelastic region 21. In this regard, the graphic display sheets 24 are not elastically stretchable or contractible and as material of the graphic display sheets 24, for example, a nonwoven fabric of thermoplastic synthetic fibers, a plastic film or a paper sheet may be used.

Referring again to FIG. 3, on the interior surface of the rear waist region 3, the barrier sheet 42 is attached to the absorbent structure 40 with a hot melt adhesive 50c. The barrier cuffs 47 of the absorbent chassis 11 respectively have proximal lateral edge portions 48 are attached to the exterior surface of the barrier sheet 42 with a hot melt adhesive (not shown). The absorbent chassis 11 is attached to the rear waist region 3 in a manner as follows. The absorbent structure 40, the barrier sheet 42 and the proximal edge portions 48 are integrally attached to the absorbent chassis 11 along the lateral edge portions 46 thereof with a hot melt adhesive (not shown). The lateral edge portions 46 are overlapped with and joined to the interior sheets 33 in the portions defining the lateral elastic regions 22 in the rear waist region 3 to have a dimension in the transverse direction B in a range of 5 to 30 mm with the hot melt adhesive 50c. In consequence, in the diaper 1 being worn by the wearer, when a force acts on the lateral elastic regions 22 in the transverse direction B and in the waist circumference direction to stretch these lateral elastic regions 22, this force acts also on the absorbent chassis 11 so that the absorbent chassis 11 may get closer to or come in close contact with the wearer's skin. Though not illustrated, a cross-sectional surface extending in the transverse direction B across the interior sheets 33 in the front waist region 2 has the same configuration as that exemplified in FIG. 3. Specifically, also in the front waist region 2 is formed with the lateral elastic regions 32 and the central inelastic region 21 and the lateral edge portions 46 of the absorbent chassis 11 are attached to the interior sheet 33 in the respective lateral elastic regions 22. Consequently, it is achieved in the front waist region 2 also that the force acting on the lateral elastic regions 22 to stretch these elastic region 22 effectively acts on the absorbent chassis 11.

In FIG. 3, assuming that the graphic display sheets 24 attached to the interior sheets 33 are formed of not a nonwoven fabric but a plastic film, the interior sheets 33 and the graphic display sheets 24 may be firmly joined to each other and these sheets should not be readily peeled off each other even if an amount of the hot melt adhesive 50b is reduced. In this case, portions of the interior sheets 33 in the lateral elastic regions 22 are firmly joined to the exterior sheets 32 in the series of seams 9 and to the plastic film of the graphic display sheets 24 with a smaller amount of the hot melt adhesive 50b. As an advantageous result of reducing the amount of the hot melt adhesive 50b used in the lateral elastic regions 22, it is possible to prevent the hot melt adhesive 50b from passing through the interior sheets 33 and coming in contact with the wearer's skin.

Figure 4:
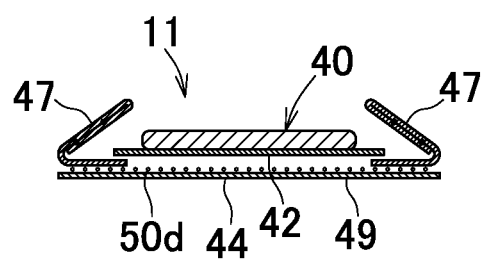
FIG. 4 is a sectional view taken along line IV-IV in FIG. 2.

Referring to FIG. 4 of a sectional view taken along line IV-IV in FIG. 2. The crotch region 4 includes the absorbent chassis 11 and the base sheet 44 attached to the barrier sheet 42 of the absorbent chassis 11 with a hot melt adhesive 50d.

Figure 5:
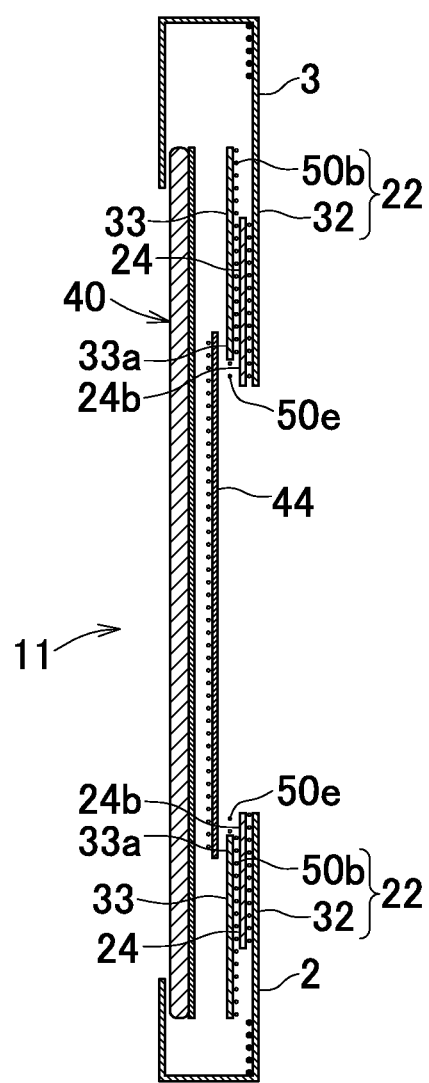
FIG. 5 is a sectional view taken along line V-V in FIG. 2.

Referring to FIG. 5 of a sectional view taken along line V-V in FIG. 2, line V-V extends in the longitudinal direction across one of the lateral elastic regions 22 in the front and rear waist regions 2, 3 in FIG. 1. The respective interior sheets 33 are joined to the exterior sheets 32 and the graphic display sheets 24 with the hot melt adhesive 50b. The exterior sheets 32 and the graphic display sheets 24 extend inwardly beyond inner edge portions 33a of the respective interior sheets 33

Figure 6:
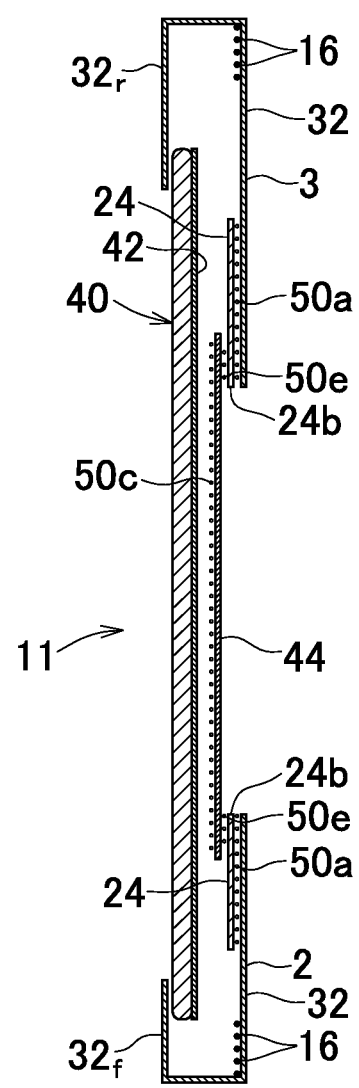
FIG. 6 is a sectional view taken along line VI-VI in FIG. 2.
Figure 7:
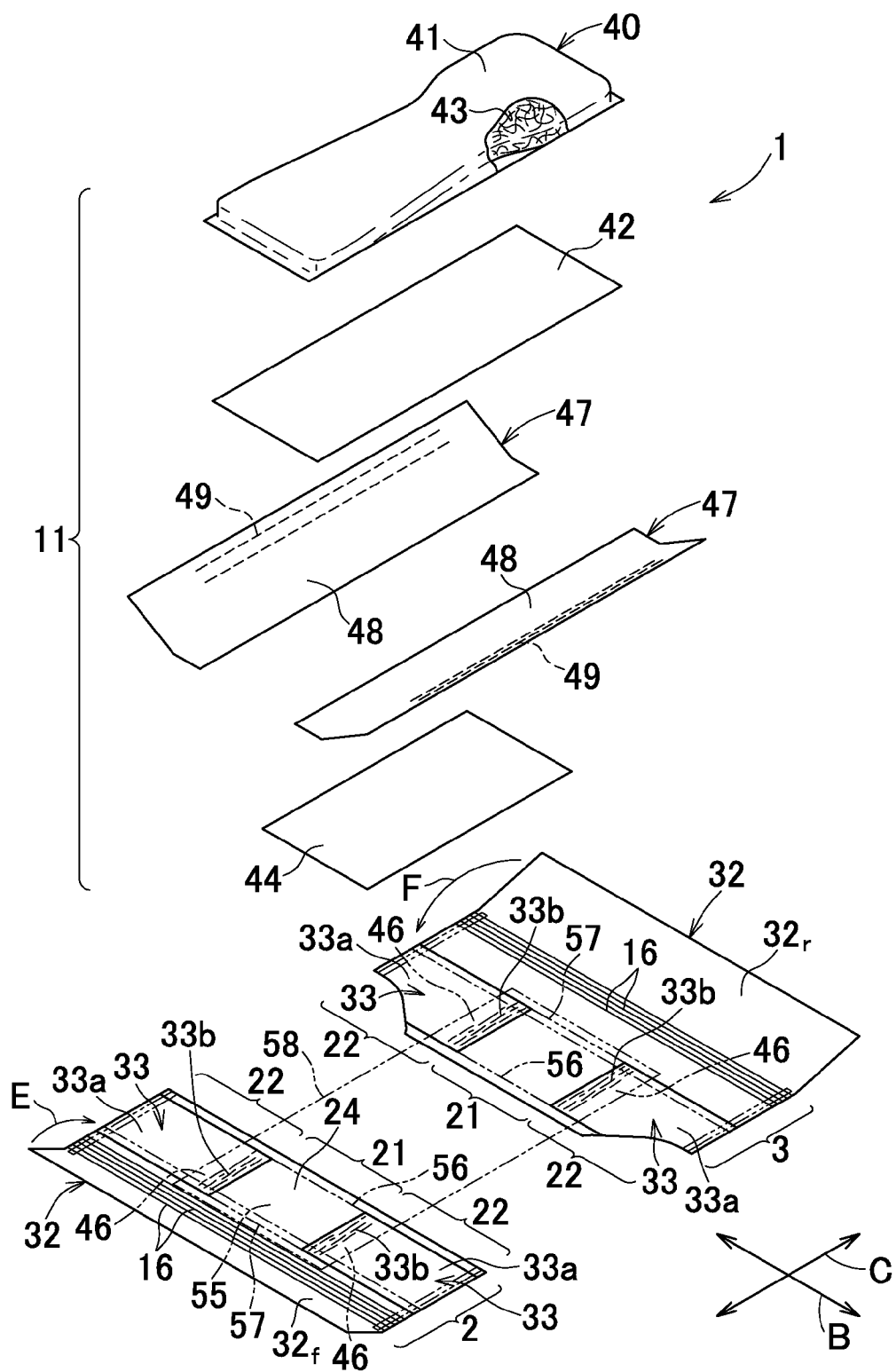
FIG. 7 is an exploded perspective view of the developed diaper.

Referring to FIG. 6 of a sectional view taken along line VI-VI in FIG. 2, line VI-VI extends in the longitudinal direction across the central inelastic region 21 in the front and rear waist regions 2, 3. In the front and rear waist regions 2, 3, the graphic display sheets 24 are attached to the interior surfaces of the respective exterior sheets 32 with the hot melt adhesive 50a and the elastics 16 also are attached to these interior surfaces with a hot melt adhesive (not shown). The graphic display sheets 24 respectively have end portions 24b adjacent to the crotch region 4 are attached to the base sheet 44 with a hot melt adhesive 50e and, in a preferred diaper 1, end portions 24b in FIG. 5 are also attached to the base sheet 44. With such an arrangement, the wearer's fingers should not be unintentionally caught between the front waist region 2 and the absorbent chassis 11 or between the rear waist region 3 and the absorbent chassis 11. In the diaper 1 in which the graphic display sheets 24 are not used or the exterior sheets 32 extend from the graphic display sheets 24 toward the crotch region 4, the exterior sheets 32 and the base sheet 44 may be joined to each other. In this regard, the diaper 1 according to the present invention may be implemented in a manner that the base sheet 44 and the graphic display sheets 24 are not joined to each other or the base sheet 44 and the exterior sheets 32 are not joined to each other. End edge portions 32f, 32r of the exterior sheets 32 folded inwardly along the periphery of the waist-opening 13 are joined to the interior sheets 33 facing these end edge portions 32f, 32r with a hot melt adhesive (not shown).

Referring to FIG. 7 of an exploded perspective view of the diaper 1, the exterior sheet 32 in the front waist region 2 is disposed with a plurality of elastics 16 and the interior sheet 33 attached thereto and the exterior sheet 32 has the end edge portion 32f illustrated to be in an obliquely rising state. The end edge portion 32f is folded toward the interior surface of the diaper in a direction indicated by an arrow E. The interior sheets 33 are located on lateral sides in the transverse direction B of the exterior sheet 32 and each of the interior sheets 33 is divided into a tensioned region 33a in a state of being elastically stretched in the transverse direction B and a relaxed region 33b released from the state of being elastically stretched in the transverse direction B. The tensioned regions 33a are attached to the exterior sheet 32 with the hot melt adhesive 50b (See FIG. 3) to form the lateral elastic regions 22. The relaxed regions 33b respectively lie adjacent to the associated lateral elastic regions 23 without being attached to the exterior sheet 32 and are formed with gathers/creases. In the front waist region 2, the relaxed regions 33b opposed to each other in the transverse direction B and a region extending between these relaxed regions 33b define the central inelastic region 21 in which the graphic display sheet 24 (See FIG. 3) is attached to the interior surface of the exterior sheet 32.

While a method for arranging the interior sheets 33 on the respective exterior sheets 32 will be described in detail later with reference to FIGS. 8 and 9, this method is briefly described here with reference to FIG. 7. An elastically stretchable first web 201 (See FIG. 8) from which the interior sheets 33 are obtained in a state of being stretched in the transverse direction B, for example, by 150 to 350% of its initial length is lapped over the exterior sheet 32 under tension in the transverse direction B in a manner that the first web 201 is joined to the regions predetermined to form the lateral elastic regions 22 of the exterior sheets 32 with the hot melt adhesive 50b but not joined to the regions predetermined to form the central inelastic region 21. Imaginary lines 56, 57 in FIG. 7 indicate lateral edges of the first web 201. Then a portion of the first web 201 predetermined to form the central inelastic region 21 is cut into two in the transverse direction B. These two portions of the first web 201 respectively contract in directions opposite to each other to form the relaxed regions 33b in the interior sheets 33. Portions of the first web 201 lying in the lateral elastic regions 22 form the tensioned regions 33a in the interior sheets 33.

The exterior sheet 32 in the rear waist region 3 illustrated in FIG. 7 forms also a portion of the crotch region 4 and disposed with a plurality of elastics 16 and the interior sheets 33. As illustrated, the exterior sheet 32 has the end edge portion 32r in an obliquely rising state. The end edge portion 32r is folded inwardly of the diaper 1 in a direction indicated by an arrow F. The interior sheets 33 are located on both lateral portions of the exterior sheet 32 and each of the interior sheets 33 is divided into the tensioned region 33a and the relaxed region 33b. The tensioned regions 33a are joined to the exterior sheet 32 with the hot melt adhesive 50b to form the lateral elastic regions 22. The relaxed regions 33b lie adjacent to the respective lateral elastic regions 22 without being joined to the exterior sheet 32 and are formed with gathers/creases. In the rear waist region 3, the region including a region extending between the relaxed region 33b and the relaxed region 33b and these relaxed regions 33b defines the central inelastic region 21. The graphic display sheet 24 is attached to the interior surface of the exterior sheet 32 in this central inelastic region 21. Such allocation of the interior sheets 33 in the rear waist region 3 is achieved in the same manner as the interior sheets 33 in the front waist region 2.

An imaginary line 58 in FIG. 7 indicates a planar shape of the absorbent chassis 11. The absorbent chassis placed on the interior surface of the front waist region 2 and the rear waist region 3 is joined to the respective lateral elastic regions 22 with the hot melt adhesive 50c (See FIG. 3) inboard of the imaginary line 58 extending in the front-back direction A. The chassis is joined also to the central inelastic region 21 with the hot melt adhesive 50c.

The diaper 1 illustrated in FIGS. 2 to 7 is folded along a transverse axis Q-Q (See FIG. 1) bisecting a dimension in the front-back direction A and the lateral edge portions 7, 8 of the front and rear waist regions 2, 3 are joined to each other along the series of the seams 9 (See FIG. 1) to obtain the diaper 1 illustrated in FIG. 1.

Figure 8:
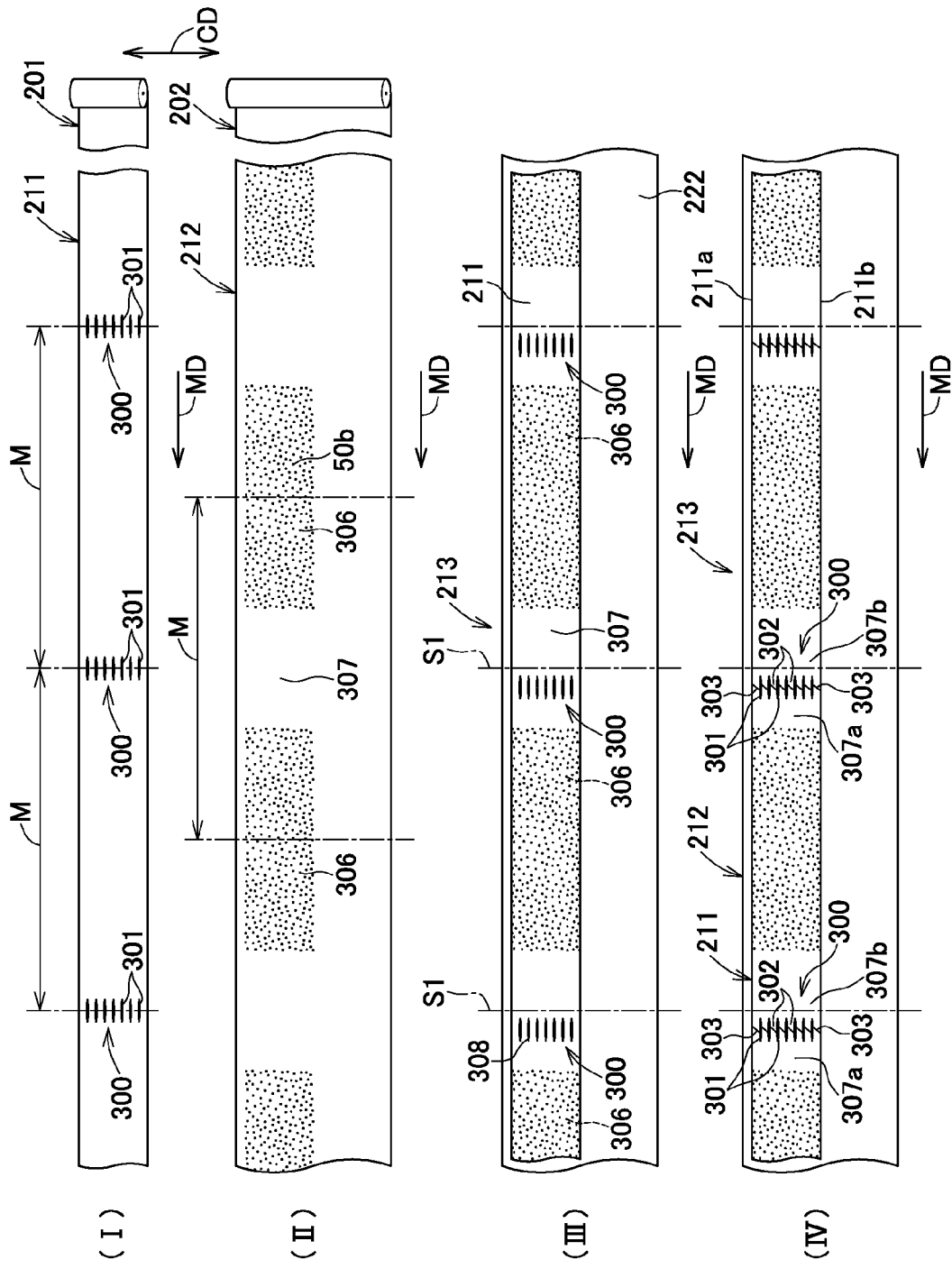
FIG. 8 (I)-(IV) is a diagram illustrating the steps of continuously manufacturing a front waist region.

FIG. 8 is a diagram illustrating a series of steps of forming the central inelastic region 21 and the lateral elastic regions 22, taking the front waist region 2 in FIG. 7 as an example.

In a step I, a first web 201 from which the interior sheet 33 is to be obtained is continuously fed in a machine direction MD. The first web 201 has the same elasticity as that of the interior sheet 33 and, in the step I, the first web 201 is fed in the machine direction MD in a state of being elongated 1.5 to 3.5 times the initial length. In the step I, the first web 201 in the elongated state is formed with a series of cut lines 300 at predetermined pitches M to obtain a first processed web 211. In each of the cut lines 300, a plurality of first cut lines 301 rectilinearly extending in the machine direction MD are arranged in a cross direction CD at predetermined intervals. The pitches M are arranged over a dimension corresponding to a transverse dimension of the diaper 1. In the first processed web 211, an interval dimension in the cross direction CD between each pair of the adjacent first cut lines 301 is remarkably reduced depending on an elongation ratio in the machine direction MD and a length of the first cut line 301. In this case, the first cut lines 301 having rectilinearly extended respectively are deformed to define oval openings 301a (See FIG. 10).

In a step II, a second web 202 from which the exterior sheet 32 is to be obtained is continuously fed in the machine direction MD under tension. The second web 202 is not as elastically stretchable as the exterior sheet 32. In the step II, regions 306 to which the hot melt adhesive 50b (See FIG. 3) are distributed are defined at predetermined pitches M and, between each pair of the adjacent regions 306, adhesive-free regions 307 are defined. In this way, a second processed web 212 is obtained. The hot melt adhesive 50b is preferably distributed at appropriate intervals to prevent the elastic elongation and contraction of the first web 201 attached to the second web 202 in a step III to be described later from being disturbed. In this regard, types of a dispenser or coater used to distribute the adhesive in this manner are not specified. A dimension in the machine direction MD of the adhesive distributed region 306 is about twice the dimension in the transverse direction of the lateral elastic region 22 in the diaper 1 illustrated in FIG. 7.

In a step III, the first processed web 211 is lapped over the second processed web 212 and these two webs 211, 212 are joined to each other with the hot melt adhesive 50b to obtain a third processed web 213. In this step, these two webs 211, 212 are properly aligned with each other so that the series of cut lines 300 may lie between each pair of the adjacent adhesive-distributed regions 306 and, more specifically, the series of cut lines 300 may lie on one side of a center line S1 bisecting the adhesive-free region 307 in the machine direction MD.

In a step IV, the third processed web 213 is formed, in regions thereof lapped over the series of cut lines 300 on the first processed web 211, with second cut lines 302 and third cut lines 303. Each of the second cut lines 302 is formed so as to intersect with each pair of the adjacent first cut lines 301 in the cross direction CD. The third cut lines 303 are formed so as to intersect with a lateral edge 211a of the first processed web 211 and the first cut line 301 lying adjacent to this lateral edge 211a and to intersect with a lateral edge 211b of the first processed web 211 and the first cut line 301 lying adjacent to this lateral edge 211b. When the second and third cut lines 302, 303 are formed in this manner, the third cut lines 303, 303 on upper and lower side as viewed in FIG. 8 are connected with each other through the first cut lines 301 and the second cut line 302 so that the first processed web 211 may be bisected in the machine direction MD. In the first processed web 211 bisected in this manner, regions 313, 314 lying on lateral sides of the series of cut lines 300 elastically contract in directions opposite to each other to vicinities of the adhesive distributed regions 306 in which the first and second processed webs 211, 212 are joined to each other.

FIG. 9 is a diagram partially illustrating a fourth processed web 214 obtained as a result of contraction of adhesive-free regions 307a, 307b having been bisected along the center line S1 in the step IV of FIG. 8 in the first processed web 211. In FIG. 9, a planar shape of the absorbent chassis 11 attached to the fourth processed web 214 is indicated by an imaginary line. In addition, a line along which the adhesive distributed region 306 is bisected in the machine direction MD is indicated by a center line S2. In such fourth processed web 214, the respective adhesive distributed regions 306 have a dimension in the machine direction M about twofold of the dimension in the transverse direction of the respective lateral elastic regions 22 in FIG. 7 and a region defined between each pair of the adjacent adhesive distributed regions has the same dimension as the dimension in the transverse direction of the central inelastic region 21 in FIG. 7. So, the absorbent chassis 11 may be placed on the fourth processed web 214 as indicated by the imaginary line, attached to the first processed web 211 in the adhesive distributed regions 306 with the hot melt adhesive 50c (See FIG. 3) and then the fourth processed web 214 may be cut along the center line S2 in the adhesive distributed region 306 to obtain a composite body in which the absorbent chassis 11 is attached to the front waist region 2 as illustrated in FIG. 7. In this composite body, the bisected adhesive distributed region 306 defines the lateral elastic regions 22, the region extending between each pair of the adjacent adhesive distributed regions 306 defines the central inelastic region 21 and the elastically contracted adhesive-free regions 307a, 307b define the relaxed regions 33b in FIG. 7. When the adhesive-free regions 307a, 307b are stretched toward a center of the central inelastic region 21, these regions 307a, 307b come in contact with each other at the region in which the series of cut lines 300 was present.

The central inelastic region 21 and the lateral elastic regions 22 in the rear waist region 3 illustrated in FIG. 7 are also obtained by following the same steps as for the front waist region 2.

The step exemplified in FIG. 8 may be adopted to form the central inelastic regions 21 and the lateral elastic regions 22 in the front waist region 2 and the rear waist regions 2 to facilitate a conveyance of the interior sheet 33 of the diaper 1 and to improve a production speed of the diaper 1 for the reason that the elastic interior sheet 33 used only in the lateral elastic regions 22 can be conveyed in a state of being placed on the second processed web 212 which is continuous material for the exterior sheets 32.

When the first processed web 211 is cut along the first to third cut lines 301 to 303, the second processed web 212 lapped over the first processed web 211 also may be formed with the second and third cut lines 302, 303, the second and third cut lines 302, 303 should not tear the first processed web 211 or form the second processed web 212 with large openings. Inconsequence, an appearance of the exterior sheet 33 and/or the graphics 24a on the graphic display sheet 24 attached to the exterior sheet 33 should not be significantly damaged. In order to avoid a situation that the presence of the second and third cut lines 302, 303 formed in the exterior sheet might be distinguished, the second and third cut lines 302, 303 are preferably formed in regions biased in the transverse direction B from the center in the transverse direction B of the central inelastic region 21, i.e., from the center in the transverse direction B of the diaper 1.

FIG. 10 is a partially scale-enlarged diagram of the third processed web 213 to exemplify the third processed web 213 in the step IV of FIG. 8. The first cut lines 301 in FIG. 10 form slits 301a each having a relatively large area. In such third processed web 213, a region between each pair of the adjacent first cut lines 301, 301, i.e., between each pair of the slits 301a, 301a has a width gradually reduced and, consequently, not only length dimensions of the second, third and fourth cut lines 302, 303, 304 can be reduced but also these cut lines 302, 303, 304 can be widely spaced apart from each other. In this case, the third processed web 213 and the fourth processed web 214 of FIG. 8 are capable of alleviating a damage of the second processed web 212 due to the second, third and fourth cut lines 302, 303, 304.

In the exemplified diaper 1, the absorbent chassis 11 should not be formed with gathers/creases due to use of the elastics and the central inelastic regions 21 in the front and rear waist regions 2, 3 can be reliably prevented from being formed with gathers/creases. Consequently, visuality of the graphics 24a on the diaper 1 is improved. Also when an indicator indicating an occurrence of urination within the diaper 1 is disposed on the interior side of the barrier sheet 42 in the absorbent chassis 11, a visuality of such indicator is assured. In this regard, it is not essential for the diaper 1 according to the present invention to use the graphic display sheets 24 and/or the indicator. In addition, the present invention may be implemented in a manner that the central inelastic region 21 and the lateral elastic regions 22 are formed in either in the front waist region 2 or in the rear waist region 3.

REFERENCE SIGNS LIST 1 diaper
2 front waist region
3 rear waist region
4 crotch region
11 absorbent chassis
21 central inelastic region
22 lateral elastic regions
24a graphics
32 exterior sheet
33 interior sheets
42 barrier sheet
46 lateral edge portions
201 first web
202 second web
211 first processed web
211a lateral edge
211b lateral edge
212 second processed web
213 third processed web
300 series of cut lines
301 first cut line
302 second cut line
303 third cut line
306 joint region (adhesive distributed region)
307 adhesive-free region
307a adhesive-free region
307b adhesive-free region
A front-back direction
B transverse direction
C longitudinal direction
MD machine direction
CD cross direction

The invention claimed is:

1. A disposable pull-on diaper having a longitudinal direction and a transverse direction being orthogonal to the longitudinal direction, including:
a front waist region;
a rear waist region;
a crotch region;
an absorbent chassis extending from the crotch region to the front and rear waist regions;
lateral elastic regions formed in at least one of the front and rear waist regions so as to be elastically stretchable in the transverse direction from lateral edges of the absorbent chassis; and
a central inelastic region defined between the lateral elastic regions and not being elastically stretchable, wherein:
at least one of the front and rear waist regions includes an exterior sheet not being elastically stretchable in the transverse direction and a pair of interior sheets lying on an interior surface side of the exterior sheet and being elastically stretchable in the transverse direction;

the absorbent chassis has an absorbent structure;

the pair of interior sheets extends from lateral edges of at least one of the front and rear waist regions to lateral edges of the absorbent structure without extending across the absorbent structure;

the interior sheets are attached under tension to the interior surface of the exterior sheet in the lateral elastic regions; and in the central inelastic region, the interior sheets are spaced apart from each other and are in an elastically relaxed state in vicinities of the respective lateral elastic regions.

2. The diaper according to claim 1, wherein the central inelastic region is formed on an exterior side of the absorbent chassis.

3. The diaper according to claim 2, wherein the absorbent chassis has lateral edge portions on lateral sides of a longitudinal axis bisecting the diaper in the transverse direction and the lateral edge portions are attached to the lateral elastic regions.

4. The diaper according to claim 2, wherein the absorbent chassis has a barrier sheet and the central inelastic region is attached to the absorbent chassis from an exterior side of the barrier sheet.

5. The diaper according to claim 2, wherein an indicator adapted to indicate an occurrence of urination within the diaper is interposed between the central inelastic region and the absorbent chassis.

6. The diaper according to claim 1, wherein the absorbent chassis has lateral edge portions on lateral sides of a longitudinal axis bisecting the diaper in the transverse direction and the lateral edge portions are attached to the lateral elastic regions.

7. The diaper according to claim 6, wherein the absorbent chassis has a barrier sheet and the central inelastic region is attached to the absorbent chassis from an exterior side of the barrier sheet.

8. The diaper according to claim 6, wherein an indicator adapted to indicate an occurrence of urination within the diaper is interposed between the central inelastic region and the absorbent chassis.

9. The diaper according to claim 1, wherein the absorbent chassis has a barrier sheet and the central inelastic region is attached to the absorbent chassis from an exterior side of the barrier sheet.

10. The diaper according to claim 3, wherein the absorbent chassis has a barrier sheet and the central inelastic region is attached to the absorbent chassis from an exterior side of the barrier sheet.

11. The diaper according to claim 9, wherein an indicator adapted to indicate an occurrence of urination within the diaper is interposed between the central inelastic region and the absorbent chassis.

12. The diaper according to claim 1, wherein an indicator adapted to indicate an occurrence of urination within the diaper is interposed between the central inelastic region and the absorbent chassis.

13. The diaper according to claim 1, wherein display graphic display sheets are attached to the interior surface of the exterior sheet and the graphics are visually recognizable from the outside of the exterior sheet.

14. The diaper according to claim 1, wherein the interior sheets are formed of elastically stretchable elastic fibrous nonwoven fabric of an elastically stretchable elastic material and an elastically non-stretchable inelastic material.

15. The diaper according to claim 1, wherein the interior sheets are formed of a nonwoven fabric of thermoplastic synthetic fibers and a plurality of rubber threads or rubber bands being contractibly attached to the nonwoven fabric under tension.

16. The diaper according to claim 1, wherein the interior sheets are formed of a thermoplastic synthetic resin film which is elastically stretchable in the transverse direction.

\* \* \* \* \*